United States Patent [19]
Tamatani et al.

[11] Patent Number: 4,971,815

[45] Date of Patent: Nov. 20, 1990

[54] ADDITIVE FOR STOCK FEEDS, STOCK FEED CONTAINING ADDITIVE, AND PROCESS FOR PREPARATION OF ADDITIVE

[75] Inventors: Hiroaki Tamatani; Kazuo Takahashi; Kazuo Sato; Kiyoshi Mizushima, all of Sunagawa; Fuminobu Yoshimi, Hokkaido; Sohei Morita, Yokohama, all of Japan

[73] Assignee: Mitsui Toatsu Chemicals, Inc., Tokyo, Japan

[21] Appl. No.: 377,124

[22] Filed: Jul. 10, 1989

Related U.S. Application Data

[62] Division of Ser. No. 201,751, Jun. 3, 1988, Pat. No. 4,865,852.

[30] Foreign Application Priority Data

Jun. 5, 1987 [JP] Japan ................................ 62-140008
Dec. 28, 1987 [JP] Japan ................................ 62-329885

[51] Int. Cl.$^5$ ................................................ A23K 1/00
[52] U.S. Cl. ........................................ 426/53; 426/518; 426/520; 426/635; 426/658; 426/807

[58] Field of Search ................... 426/635, 2, 53, 61, 426/520, 518, 658, 807; 127/30, 39, 43

[56] References Cited

U.S. PATENT DOCUMENTS

| | | | |
|---|---|---|---|
| 4,421,852 | 12/1983 | Hoehn et al. | 127/43 |
| 4,613,377 | 9/1986 | Yamazaki et al. | 127/39 |
| 4,734,402 | 3/1988 | Hashimoto et al. | 426/2 |

Primary Examiner—R. B. Penland
Attorney, Agent, or Firm—Birch, Stewart, Kolasch & Birch

[57] ABSTRACT

An additive for stock feeds containing decomposition products of chicory roots in which the total content of polysaccharides and inulooligosaccharides of tri- and higher saccharides obtained by decomposing the chicory roots is 40% by weight or more of the total solids content and is 80% by weight or more of the total saccharides. The stock feed preferably contains 0.1 to 10% by weight of the additive. The additive is prepared by a process which comprises the steps of chopping and then heating/drying chicory roots in order to form chicory flakes, and grinding the chicory flakes, or by a process which comprises the step of enzymatically decomposing the chicory roots without an extraction step.

8 Claims, No Drawings

ADDITIVE FOR STOCK FEEDS, STOCK FEED CONTAINING ADDITIVE, AND PROCESS FOR PREPARATION OF ADDITIVE

This application is a divisional of copending application Ser. No. 07/201,751, filed on June 3, 1988 U.S. Pat. No. 4,865,852.

BACKGROUND OF THE INVENTION (1) Field of the Invention

The present invention relates to an additive for stock feeds, a stock feed containing said additive and a process for the preparation of the additive. When added to livestock feed, the additive of the invention prevents diarrhea in stock and contributes to an increase in the body weight of the stock and the efficient utilization of the feed.

(2) Description of the Prior Art

In recent years, the demand for edible meat has increased, and breeders of stock strongly desire an efficient stock breeding technique. Today, in the field of stock farming, much attention is paid to the efficient production of the stock, and consequently there is the tendency that the greatest possible number of stock are bred to a limited extent, which often leads to a bad breeding environment. In particular, diarrhea in infant stock during the weaning period has an undesirable influence on their increase in body weight, and in some cases, unfortunately, the stock die. Furthermore, the incomplete development of the stock in their infancy causes the growing period to drag on, so that the efficiency of the stock feed deteriorates and thus profit diminishes.

Accordingly, in order to inhibit the problem of diarrhea and loose passage in the stock, particularly infant stock, stock feeds containing an antibiotic are employed, but the effect of the antibiotic is not considered to be sufficient. In addition, for the prevention of diarrhea, use of various lactic bacteria and/or bifido bacteria has been tried.

Another method has been developed in which an additive prepared by subjecting the starting material milk whey to various treatments is added to the stock feed so as to multiply the number of microorganisms present in the alimentary canal of animals.

The addition of an oligosaccharide to the stock feed has been reported in Japanese Patent Unexamined Publication Nos. 51-118827 and 60-34134.

In Japanese Patent Unexamined Publication No. 52-151787, an agent is disclosed which is prepared by mixing lactose with bifido bacteria. This agent heightens the existence ratio of the bacteria during the storage of the stock feed or in the intestines of the stock.

A conventional technique regarding the stock feed containing an oligosaccharide is disclosed in Japanese Patent Unexamined Publication No. 61-40754.

Some of the products industrially obtained through the above-mentioned methods are on the market, but it is not believed that their effects are sufficient. In order to prevent diarrhea and to efficiently increase the body weight of the stock, there still remain some problems to be solved.

In certain cases, a dosed live bacteria agent is not stably present in the intestines of the stock. In the method of using the oligosaccharide, as disclosed in Japanese Patent Publication No. 60-34134 mentioned above, the manufacturing cost of an additive containing the oligosaccharide is high, which is unprofitable from a commercial viewpoint.

In conclusion, an additive which inhibits diarrhea and effectively increases the weight of the stock has not been developed on a commercial sale.

The inulooligosaccharide disclosed in Japanese Patent Unexamined Publication No. 61-40754 is composed mainly of inulobiose ($F_2$), inulotriose ($F_3$), inulotetraose ($F_4$), inulopentaose ($F_5$) or inulohexaose ($F_6$). However, since this inulooligosaccharide is obtained by decomposing inulin with oxalic acid, it mainly contains inulobiose or inulotriose, and does not include many high molecular weight inulosaccharides. Therefore, the inulooligosaccharide disclosed in this publication is not satisfactory for heightening the effectiveness of the stock feed. Furthermore, the raw material from which this inulooligosaccharide is derived is jerusalem artichoke, and, therefore, there is yet another drawback in that the stock do not eat the feed containing it willingly.

Usually, the inulooligosaccharide has excellent characteristics, and for example, it can activate macrophages, develop bifido bacteria, and decrease fat content in the stock. These characteristics are more remarkable in the high molecular weight oligosaccharides than in the low molecular weight oligosaccharides.

It is known that inulin is present in chicory roots. Chicory flakes are utilized as a filler for coffee. Inulin is a polysaccharide in which 35 fructose moieties are linked via a $\beta$-2,1 bond, and it has a molecular weight of about 5,400 and carries glucose at the terminal thereof.

The usual inulooligosaccharide can be defined as an oligosaccharide in which 3 to 6 fructose moieties are linked to each other via the $\beta$-2,1 bond, and it is generally composed of inulotriose ($F_3$), inulotetraose ($F_4$), inulopentaose ($F_5$) or inulohexaose ($F_6$).

The inulooligosaccharide may be prepared by a known method, for example, a method of partially decomposing inulin with a dilute acid as described above, or another method of first extracting inulin from a specific plant with warm water, and treating the extracted liquid with an endo-type inulase.

However, these methods are not preferable, because vegetable fiber and trace components which exist in the raw material are lost.

An additive for stock feed which is prepared by directly utilizing decomposition products of a plant containing inulin without removing the vegetable fiber and trace components therefrom is not known. Also, there are not known either a stock feed containing such an additive or a method for preparing this new additive.

SUMMARY OF THE INVENTION

According to the present invention, there are provided an additive for stock feeds which is prepared from chicory roots and which can protect livestock from diarrhea and can increase the body weight of the livestock efficiently, a method for preparing the new additive, and a livestock feed containing the additive.

The first aspect of the present invention is directed to an additive for stock feed containing decomposition products of chicory roots in which the total content of inulooligosaccharides of tri- and higher saccharides obtained by decomposing the chicory roots and polysaccharides is 40% by weight or more of the total solids content and is 80% by weight or more of the total saccharides.

The decomposition of the chicory roots may be carried out by heating and drying the chopped chicory roots. Furthermore, the decomposition may be performed by first chopping and grinding the chicory roots into fine pieces, then preparing a slurry of the pieces, and directly enzymatically decomposing the slurry; or alternatively by first chopping the chicory roots into fine pieces, then heating and drying them, adding thereto water to form a slurry, and directly enzymatically decomposing the slurry.

The second aspect of the present invention is directed to a stock feed containing 0.1 to 10% by weight of the aforesaid additive for stock feeds.

The third aspect of the present invention is directed to a method for preparing an additive for stock feeds which comprises the steps of chopping and heating and drying chicory roots to form chicory flakes, and then grinding the chicory flakes.

The fourth aspect of the present invention is directed to a method for preparing an additive for stock feeds which comprises the steps of first chopping and grinding chicory roots to form a slurry, or adding water to chicory flakes preparing by chopping and then heating and drying the chicory roots in order to form a slurry, adding an endo-type inulase to the slurry, and enzymatically decomposing the slurry at 40° to 60° C. for 12 to 36 hours.

DETAILED DESCRIPTION OF THE INVENTION

An object of the present invention is to provide an additive for stock feeds which contains an effective amount of inulooligosaccharides of high molecular weight components effective to inhibit diarrhea in livestock and to increase the body weight of the stock efficiently, and which further contains vegetable fiber and trace components.

Another object of the present invention is to provide a stock feed containing the aforesaid additive.

Still another object of the present invention is to provide a method for preparing said additive for stock feed at a low cost.

As a result of extensive research, the present inventors have found that when chicory roots, which are part of an inulin-containing plant, are chopped and then heated and dried under suitable conditions, the inulin present in the chicory roots is partially decomposed to produce an inulooligosaccharide, and that the inulooligosaccharide can activate macrophages, multiply bifido bacteria and decrease fat in the stock. In addition, the inventors have found that when the inulooligosaccharide prepared by directly decomposing the chicory roots with an endo-type inulase enzyme is added to a stock feed, diarrhea in infant stock can be inhibited sufficiently, and thus the growth of the stock can be facilitated.

The chicory roots used in the present invention are roots of the plant containing inulin called chicory. The amount of impurities such as colorant substances and salts is less in chicory roots than in the jerusalem artichoke, which was known in the past as the plant containing inulin. This fact is a special feature of the chicory roots.

With regard to chicory roots and the jerusalem artichoke, examples of compositions of their extracts with warm water are as follows:

|  | Chicory | Artichoke |
| --- | --- | --- |
| Solids Content (%) | 26.1 | 25.6 |

-continued

|  | Chicory | Artichoke |
| --- | --- | --- |
| Electric Transmission (μs/cm) | 7,500 | 12,000 |
| Coloring Degree | 27 | 133 |
| Ash (% to solids content) | 4.6 | 5.9 |
| Saccharides (% to solids content) | 70.0 | 68.3 |

Jerusalem artichokes containing a significant amount of impurities are not eaten willingly by the stock, and therefore Jerusalem artichokes are not a preferred raw material source for the inulooligo-saccharide.

The inulooligosaccharide used in the present invention is an oligosaccharide in which fructoses are linked to each other by a $\beta$-2,1 bond. Such fructoses include inulotriose ($F_3$), inulotetraose ($F_4$), inulopentaose ($F_5$) and inulohexaose ($F_6$).

The decomposition of the inulin present in the chicory roots into the inulooligosaccharide may be carried out by chopping and then heating and drying the chicory roots.

When the heating temperature in the heating and/or drying step is too high, or when the heating temperature is held for an excessively long time, the inulooligosaccharide is further decomposed into lower molecules, so that its effectiveness in the stock feed deteriorates and its coloring properties increase. Therefore, the heating conditions should be such that the total content of polysaccharides and the inulooligosaccharides of tri- and higher saccharides is 40% or more of the total solids content and comprises 80% or more of the total saccharides. To satisfy the above-mentioned heating conditions, it is preferred that the temperature is in the range of 120° to 250° C., the heating time is in the range of 8 to 24 hours, and the product of the temperature and the time is in the range of 1,500 to 3,000 (°C. × hour).

In the above heating conditions, a temperature of 180° C. and heating time of 12 hours are optimum. When the temperature is lower and when the heating time is shorter than the above-mentioned levels, the decomposition of inulin is insufficient. Inversely, when these factors are higher and longer than the above-mentioned levels, lower molecules are formed, the effectiveness as stock food degrades, and the coloring factor rises inconveniently. The use of the product of the temperature and time as a guide means that if the temperature is high, the heating time should be short, and that if the heating time is long, the temperature should be low.

The chicory materials used in the present invention include chicory roots or chicory flakes which may be prepared by chopping and drying the chicory roots without heating. The additive in the present invention may be prepared by chopping and/or by heating and drying these materials. The composition of the heated and dried chicory flakes as used in the present invention is, for example, as follows:

| Solids Content | about 90% |
| --- | --- |
| Inulin (nona-and higher saccharides) | 50.4% (to solids content) |
| Oligosaccharides (tri- to octasaccharides) | 15.0% (to solids content) |
| Free Saccharides (Fru) | 0.9% (to solids content) |
| Free Saccharides (Glu) | 0.1% (to solids content) |
| Free Saccharides (Suc) | 3.6% (to solids content) |

The heated and dried chicory flakes used in the present invention originally contain at least 10 weight % or more, suitably no less than about 15% by weight, of the inulooligosaccharide in the solids content thereof. In addition, the inulin in the chicory flakes has a low molecular weight, and therefore the enzyme decomposition of the inulin is conveniently easy. That is to say, the inulin (nona- and higher saccharides) a shown in the above table is different from the inulin that is originally present in chicory roots.

Furthermore, the heated and dried chicory flakes contain fibrous materials, proteins and the like derived from the chicory roots. According to the calculation of the data in the above table, the total content of the inulooligosaccharide of the tri- and higher saccharides is 15% by weight with respect to the solids content which is at least 10% by weight, the total content of the polysaccharides and the inulooligosaccharide of the tri- and higher saccharides is 65.4% by weight with respect to the solids content which is higher than 40% by weight, and the total content of the saccharides is 93.4% by weight which is higher than 80% by weight. Various analyses for the heated/dried chicory flakes support these data.

In chicory roots, an exo-type inulase is present, and while the chicory roots are being preserved, the inulin in the roots is decomposed gradually by this enzyme to form fructose. If such a heat treatment as described above is previously made, the exo-type inulase can be deactivated to minimize the production of fructose.

The saccharides and other components present in the chicory flakes are as follows:

| Solids Content | about 90% |
| --- | --- |
| Saccharides | |
| Mono- and disaccharides | 5% (to solids content) |
| Tri- to octasaccharides | 15% (to solids content) |
| Nona- and higher saccharides | 50% (to solids content) |
| Fibrous Substances | 12% (to solids content) |
| Protein | 12% (to solids content) |
| Ash | 5% (to solids content) |
| Fat | 1% (to solids content) |

The chicory flakes obtained in the above-mentioned manner can be directly used as the additive for stock feed.

The chopped chicory roots or the chicory flakes prepared by the above thermal decomposition may be further enzymatically decomposed.

In the case that the thus prepared chicory flakes are used as the raw material in the present invention, a product can be obtained which contains a large amount of the inulooligosaccharide having a polymerization degree of 3 to 7. Therefore, the method of using the chicory flakes is more preferable than the method of performing the enzymatic decomposition immediately after chopping of the chicory roots, because the chicory flakes contain no less than 15% by weight of the inulooligosaccharide, as shown in the above table.

The enzymatic decomposition is carried out according to the following procedure. First, the chicory roots are chopped and ground to prepare a slurry, or alternatively the chicory flakes are finely ground and then mixed with water to prepare a slurry, or they are roughly ground and mixed with hot water, followed by stirring to prepare a slurry. If necessary, a further treatment may be conducted by the use of pectinase and/or cellulase. Afterward, an endo-type inulase is added to the slurry, and the enzymatic decomposition is then performed at a temperature of 40° to 60° C. for 12 to 36 hours, so that a product is obtained in which 50 weight % or more of the solids content comprises the inulooligosaccharide.

Usable examples of the endo-type insulase include enzymes produced by mold fungi such as those of the genus *Aspergillus* (*A. niger* and the like) and those of the genus *Penicillium* (*P. trzebinskii* and the like), and bacteria such as *Bacillus* (*B. circulans* and the like). In a preferable case, the endo-type inulase wherein the optimum temperature is from 30° to 60° C. and the optimum pH is from 4 to 7 is used, so that the inulooligosaccharide is effectively produced from the chicory flakes. In the practical enzyme decomposition, it is preferable that the temperature of the enzymatic decomposition is high for the sake of preventing contamination with various bacteria. Therefore, the enzymatic decomposition is suitably performed at a temperature of 40° to 60° C., as described above. With regard to the ratio of endo-inulase to exo-inulase, if an enzyme solution of I/S>10 (I being the inulin-decomposing activity and S being the sucrose-decomposing activity) is used, the amount of the produced fructose can be decreased.

The above-mentioned sucrose-decomposing activity (S activity), i.e., the exo-type inulase activity, may be measured in the following manner.

An enzyme is first added to a 0.75% sucrose solution containing an acetic acid buffer solution of pH 5.0, and the reaction is then performed at 50° C. for 30 minutes in order to form a reducing sugar. Thereafter, the reducing sugar is quantitatively analyzed by a 3,5-dinitrosalicylic acid process and the activity is obtained on the basis of the analyzed value. An enzyme unit is represented by the amount of enzyme which can produce 2 $\mu$mole of the reducing sugar for 1 minute in 1 ml of a culture medium.

The inulin-decomposing activity (I activity), i.e., the endo-type inulase activity, can be obtained by means of the same procedure as in the above measurement of the S activity with the exception that a 0.75% inulin solution is employed. However, an enzyme unit of the I activity is the amount of enzyme which can produce 1 $\mu$mole of a reducing sugar.

The endo-type inulase activity ratio of the enzyme solution can be represented by the ratio (I/S) of the above-mentioned S and I activities, and when the enzyme solution of I/S>10 is used, it is possible to reduce the production of fructose.

The additive of the present invention has a total content of polysaccharides and inulooligosaccharides of tri- and higher saccharides of 40% or more by weight of the total solids content and 80% or more by weight of the total saccharides, and furthermore includes the fibrous substances and trace components that were originally present in the chicory roots.

The additive of the invention is prepared by chopping and then heating and/or drying chicory roots, wherein the additive includes nona- and higher saccharides in an amount of at least 30 weight % to no more than 50 weight %, and oligosaccharides (tri- to octasccharides) of at least 10 wt. %, to no more than 15 wt. % based on the total solids content. This additive has the advantage that it is easy to manufacture at low cost.

The additive of the invention can also be prepared by the following process. The chicory roots are chopped and ground to prepare a slurry (water is not always added in the grinding step, but the addition of water is acceptable), or the above-mentioned chicory flakes are finely ground, followed by adding water thereto in order to prepare a slurry. Afterward, this slurry is directly enzymatically decomposed, thereby obtaining a crude oligosaccharide in which tri- to octasaccharides are mainly contained in an amount of about 60% by weight. The thus obtained crude oligosaccharide further can contain fibrous substances and trace components that were originally present in the chicory roots.

The oligosaccharides in which the tri- to octasaccharides are contained in large quantities can be used as the additive for stock feeds without any further treatment, but this oligosaccharide may be mixed with a material prepared by grinding and drying the chicory roots in an ordinary manner or an additive for stock feeds prepared by heating and/or drying the chicory roots in accordance with the present invention, so that the additive for stock feeds can be obtained in which the tri- to octasaccharides are contained therein in an amount of 30 to 60% by weight.

The additive may be mixed with a stock feed in an amount of 0.1 to 10% by weight in order to prepare a feed for infant stock. When the content of the additive is less than 0.1% by weight, the effect of the additive is not appreciated, and when it is in excess of 10% by weight, the cost rises disadvantageously.

The additive for stock feeds of the present invention contains a significant amount of the inulooliogosaccharide in which effective high molecular weight components are present in large quantities, and it further contains vegetable fiber and protein derived from the chicory roots. Therefore, when the feed containing the additive is fed to the stock, diarrhea in infant stock can be effectively prevented by functions of the inulooligosaccharide such as macrophage activation, multiplication of bifido bacteria in the intestines and a decrease in the fat in the stock bodies, with the result that the weight of the stock increases effectively and, thus, the feed demand ratio (the weight of feed needed to increase the unit weight of the stock) can be lowered.

In the additive prepared by directly decomposing the slurry of the chopped and ground chicory roots or the aqueous slurry of the finely ground chicory flakes, the effective inulooligosaccharide of tri- to octasaccharides is present in a noticeably high ratio, and vegetable fibers and trace components such as proteins derived from the chicory roots are still contained therein. In the present invention, there is neither any loss during extraction nor an increase in cost as in the case wherein inulin is extracted with warm water. Moreover, there is not the disadvantage that the amounts of fructose and low molecular weight oligosaccharides increase as in the case wherein a partial decomposition is performed with a dilute acid. As a result, the additive of the present invention is industrially profitable.

In the present invention, the method of heating and drying the chicory roots is achieved merely by chopping, heating/drying and grinding the chicory roots. Accordingly, the manufacturing cost is very low. Furthermore, the method of directly decomposing the slurry with an enzyme does not require any extraction of inulin, decolorization and desalting, and according to this method, the inulooligosaccharide containing a larger amount of high molecular weight components can be effectively obtained at low cost.

EXAMPLES

The present invention will now be described in detail with reference to the following examples, however, these examples are not intended to restrict the scope of the present invention.

EXAMPLE 1

First, 30 kg of chicory roots were chopped into pieces having a diameter of about 5 cm, and these pieces were then dried at 180° C. for 12 hours in a dryer in order to form 8 kg of chicory flakes. In the flakes, the solids content was 92.1% and saccharides were present in an amount of 65.4% of the solids content. The composition of the saccharides is set forth in Table 1. The results in this table indicate that the contents of monosaccharide and disaccharide components are low.

TABLE 1

| (Composition of Saccharides in Chicory Flakes) | |
|---|---|
| Monosaccharide (Glc, Fru) | 1.2 wt. % |
| Disaccharide (Suc, inulobiose) | 2.2 wt. % |
| Trisaccharide | 4.8 wt. % |
| Tetrasaccharide | 5.4 wt. % |
| Pentasaccharide | 7.6 wt. % |
| Hexa- to octasaccharides | 23.3 wt. % |
| nona- and higher saccharides | 55.4 wt. % |

The thus formed chicory flakes were ground and dried in order to prepare an additive for stock feed according to the present invention. When used, this additive will be added to the usual feed in an amount of 0.1 to 10% by weight.

For tests, three-week-old baby pigs were fed with feeds containing 1% by weight and 5% by weight of the additive of the present invention and a feed containing no additive. Each group of 6 pigs was allowed to grow for 4 weeks, and thereafter, the average weight increment, feed demand ratio and occurrence of diarrhea were inspected. The results are set forth in Table 2.

TABLE 2

| Amount of Additive (%) | Average Weight Increment (kg) | Feed Demand Ratio | Occurrence of Diarrhea |
|---|---|---|---|
| 0 | 9.3 | 1.6 | ++ |
| 1 | 10.7 | 1.5 | − |
| 5 | 12.1 | 1.4 | − |

++: Very often
−: Very little

As is apparent from the above results, with regard to the pigs to which the additive of the present invention was fed, the average weight increments are 1.1 to 1.3 times as much as those of the pigs to which no additive had been fed, and the feed demand ratios are also lower. In addition, the occurrence of diarrhea is much less than in the pigs having no additive in the feed.

EXAMPLE 2

To finely ground chicory flakes (which had passed through 32 mesh) were added 25 liters of water to prepare a slurry containing about 20 wt. % of solids content. Then, 36,000 units (1 unit is represented by the amount of enzyme which will form 1 μmole of a reducing sugar at 50° C. at a pH of 5 for 1 minute in an inulin substrate) of an endo-type inulase produced by culturing *Penicillium trzebinskii* (FERM P-8706) was added to the slurry, and enzymatic decomposition was performed at 50° C. for 12 hours. Afterward, dehydration, drying and grinding followed in order to obtain 5.5 kg of an inulooligosaccharide additive of the present invention.

The composition of the thus obtained additive is set forth in Table 3. The results in this table indicate that the main components of the additive are tri- to heptasaccharides and that the content of monosaccharide is low.

TABLE 3

| (Composition of Additive) | |
| --- | --- |
| Monosaccharide (Glc, Fru) | 3.0% |
| Disaccharide | 7.3% |
| Trisaccharide | 22.9% |
| Tetrasaccharide | 21.5% |
| Pentasaccharide | 23.2% |
| Hexa- and heptasaccharides | 18.6% |
| Octa- and higher saccharides | 3.5% |

Generally, the additive of the present invention is added to a usual feed in an amount of 0.1 to 10% in order to prepare a stock feed.

In this example, the additive was added to a stock feed in an amount of 0.1 to 5%, and, each group of 10 weaned baby pigs was allowed to grow for 30 days by the use of the additive-containing feed.

The results are set forth with average values in Table 4.

TABLE 2

| (Growth Test Results of Baby Pigs) | | | |
| --- | --- | --- | --- |
| Amount of Additive (%) | Average Weight Increment (kg) | Feed Demand Ratio | Occurrence of Diarrhea |
| 0 | 1.0 | 1.0 | ++ |
| 0.1 | 1.1 | 0.92 | + |
| 0.5 | 1.2 | 0.85 | − |
| 1.0 | 1.1 | 0.88 | − |
| 5.0 | 1.2 | 0.88 | − |

++: Very often
+: Little
−: Very little

As is apparent from the results in Table 4, with regard to the pigs to which the additive of the present invention had been fed, the body weight increments are greater than in the pigs having no additive, and the feed demand ratios are also lower. Furthermore, it is definite that the occurrence of diarrhea is inhibited remarkably by the additive.

For another test, the additive prepared above was also applied to calves.

Four groups each having six 2 to 3-week old calves were allowed to grow for 50 days. One group was fed with a commercially available milk without any additive, and the other groups were fed with stock feeds containing the additive of the present invention in amounts of 0.1 to 5%. Weight increments and feed demand ratios were calculated from the weights of the calves and the intake of the stock feeds before and after the test, and blood was sampled at certain intervals to note the amounts of cholesterol in the blood.

As a result, in the groups of calves to which the additive of the present invention had been fed, the body weight increments were 1.1 to 1.3 times, the feed demand ratios were 0.87 to 0.96 time, and the amounts of cholesterol were 0.72 to 0.90 time as much as in the calf group without any additive. Accordingly, it can be concluded that when the stock feed containing the additive of the present invention is fed to calves, their growth can be facilitated and the meat quality can be improved owing to the decrease in the fat.

EXAMPLE 3

As described hereinbefore, the inulooligosaccharide contained in the stock feed disclosed in Japanese Patent Unexamined Publication No. 61-40754 is prepared by decomposing a jerusalem artichoke raw material with oxalic acid and filtering the material to remove vegetable fiber therefrom. However, the thus obtained inulooligosaccharide contains many salts and impurities, and therefore it is not eaten by stock willingly.

Now, for the comparison of the jerusalem artichoke and chicory roots, a test was made.

Each of the crude oligosaccharide powders prepared by directly enzymatically decomposing the chicory roots and jerusalem artichoke was added to a commercially available stock feed for baby pigs in an amount of 0.5% by weight, and the respective stock feeds were fed to the baby pigs.

Three groups each having three 4-week-old baby pigs were tested. That is, the crude oligosaccharide prepared from the chicory roots was fed to the first group, the crude oligosaccharide prepared from the jerusalem artichoke was fed to the second group, and no oligosaccharide was fed to the third group. Each stock feed was fed freely thereto for 10 days, and the intakes of the stock feeds were recorded. This test was repeated 3 times.

Comparison was made on the basis of average values of the three tests. When the intake of the stock feed without any crude oligosaccharide was regarded as 100, the intake of the chicory group was 120, and that of the artichoke group was 102. This result indicates that the stock feed containing the chicory oligosaccharide is eaten more willingly by the stock than the feed containing the artichoke oligosaccharide. Therefore, it can be concluded that the chicory roots are more excellent and beneficial that the jerusalem artichoke as the raw material.

The invention being thus described, it will be obvious that the same may be varied in many ways. Such variations are not to be regarded as a departure from the spirit and scope of the invention, and all such modifications as would be obvious to on skilled in the art are intended to be included within the scope of the following claims.

What is claimed is:

1. An additive for stock feeds consisting essentially of decomposition products of chicory roots selected from products obtained by heating and drying chopped chicory roots; products obtained by first chopping and grinding chicory roots into fine pieces, preparing a slurry of the pieces, and enzymatically decomposing the slurry; and products obtained by first chopping the chicory roots into fine pieces, heating and drying the fine pieces, adding water thereto to form a slurry, and enzymatically decomposing the slurry, in which the total content of inulooligosaccharides of tri- and higher saccharides and polysaccharides obtained by decomposing said chicory roots is 40% by weight or more of the total solids content and is 80% by weight or more of the total saccharides, wherein said stock food contains 0.1 to 10% by weight of said additive.

2. A composition consisting essentially of an additive which comprises decomposition products of chicory roots selected from product obtained by heating and drying chopped chicory roots; products obtained by first chopping and grinding chicory roots into fine pieces, preparing a slurry of the pieces, and enzymatically decomposing the slurry; and products obtained by first chopping the chicory roots into fine pieces, heating and drying the fine pieces, adding water therein to form a slurry, and enzymatically decomposing the slurry, in which the total content of inulooligosaccharides of tri- and higher saccharides and polysaccharides obtained by decomposing said chicory roots is 40% by weight or more of the total solids content and is 80% by weight or more of the total saccharides, wherein said composition is a stock feed and wherein said composition contains 0.1% to 10% by weight of said additive.

3. A composition according to claim 2, wherein the additive is prepared by enzymatically decomposing a slurry of chopped and ground chicory roots without extracting inulin.

4. A composition according to claim 3, wherein the additive is prepared by enzymatically decomposing a slurry of chicory flakes obtained by chopping and then heating and/or drying chicory roots without extracting inulin.

5. An additive for stock feeds, wherein said additive is prepared by enzymatically decomposing a slurry of chopped and ground chicory roots without extracting inulin.

6. An additive for stock feeds which is prepared by mixing chicory flakes obtained by chopping and then heating and/or drying chicory roots with the additive for stock feeds of claim 5.

7. An additive for stock feeds, wherein said additive is prepared by enzymatically decomposing a slurry of chicory flakes obtained by chopping and then heating and/or drying chicory roots without extracting inulin.

8. An additive for stock feeds which is prepared by mixing chicory flakes obtained by chopping and then heating and/or drying chicory roots with the additive for stock feeds of claim 7.

* * * * *